United States Patent [19]

Harris

[11] 4,351,968

[45] Sep. 28, 1982

[54] PRODUCTION OF ORGANIC COMPOUNDS

[75] Inventor: John F. Harris, Cambridge, England

[73] Assignee: FBC Limited, Hauxton, England

[21] Appl. No.: 186,556

[22] Filed: Sep. 12, 1980

[30] Foreign Application Priority Data

Sep. 14, 1979 [GB] United Kingdom ............... 7931996
Dec. 28, 1979 [GB] United Kingdom ............... 7944469

[51] Int. Cl.³ ..................... C07C 39/10; C07C 37/56
[52] U.S. Cl. ................................. 568/763; 568/771; 568/803; 568/805
[58] Field of Search ............... 568/770, 771, 763, 803, 568/800, 805

[56] References Cited

U.S. PATENT DOCUMENTS 3,585,243 6/1971 Gradeff ............................ 568/771
3,600,446 8/1971 Massie ............................. 568/771

OTHER PUBLICATIONS

Dakin, American Chemical Journal, vol. 42, pp. 477–487 (1909).
Dankin "Organic Synthesis Collective Volume" vol. 1, pp. 149–153.

Primary Examiner—Werren B. Lone
Attorney, Agent, or Firm—Wenderoth, Lind & Ponack

[57] ABSTRACT

Pyrogallol, and analogues thereof having an alkyl, carboxy or alkoxycarbonyl substituent in the benzene ring, and their salts, are prepared by oxidizing, preferably by hydrogen peroxide, the corresponding compounds in which 1 or 2 of the OH groups are replaced by —$COR^5$ groups where $R^5$ represents hydrogen, alkyl or phenylalkyl. The production of intermediates is also described and some of these are novel.

9 Claims, No Drawings

4,351,968

PRODUCTION OF ORGANIC COMPOUNDS

This invention relates to a process for preparing pyrogallol compounds, to a process for preparing intermediates in this production, and to intermediates themselves.

Pyrogallol, 1,2,3-trihydroxybenzene, has various uses, for instance as a photographic developer, in dyeing leather and wool, in the analysis of heavy metals and as an intermediate. At present, all the pyrogallol available in commerce is prepared by decarboxylation of gallic acid obtained from comparatively rare plant sources. This makes pyrogallol expensive and difficult to procure. We have now discovered a much improved process for the preparation of pyrogallol and its analogues, which avoids such rare plant sources and produces the desired product surprisingly easily.

Accordingly, the invention provides a process for preparing a pyrogallol compound of formula

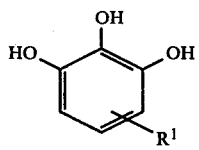

or a salt thereof, where $R^1$ represents a hydrogen atom, alkyl, carboxy or alkoxycarbonyl; which process comprises oxidising a carbonyl compound of formula

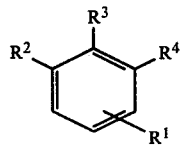

or a salt thereof, where $R^2$, $R^3$ and $R^4$ are the same or different and each represents —OH or —COR$^5$, at least one of $R^2$, $R^3$ and $R^4$ representing —OH and at least one of $R^2$, $R^3$ and $R^4$ representing —COR$^5$, where $R^5$ represents a hydrogen atom, alkyl or phenylalkyl.

The invention also provides a process for preparing pyrogallol or a salt thereof, which process comprises reacting a pyrogallol compound of formula

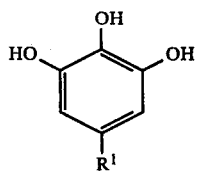

or a salt thereof,
where $R^1$ represents alkyl, with phenol, or a salt thereof, in the presence of a dealkylation catalyst.

The invention also provides a process for preparing pyrogallol or a salt thereof, which process comprises reacting the pyrogallol compound of formula III, or a salt thereof, with sulphuric acid, p-toluenesulphonic acid, ferric chloride, acid activated Fullers' Earth, aluminium chloride or zinc chloride.

The invention provides also a process for preparing 2-hydroxyisophthalaldehyde or a salt thereof, which process comprises:

(a) reacting a 2,6-dimethyl compound of formula

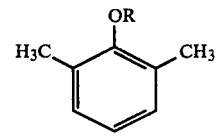

where R represents a protectant group, to oxidise the CH$_3$ groups to CHO and to convert the OR group to OH;

(b) reacting a 2,6-bis(dichloromethyl) compound of formula

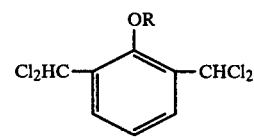

where R represents a protectant group, to hydrolyse the dichloromethyl groups and to convert the OR group to OH; or (c) reacting a 2,6-bis(chloromethyl) compound of formula

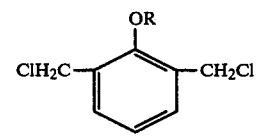

where R represents a protectant group, to convert the chloromethyl groups to CHO groups and to convert the OR group to OH.

The invention provides as new compounds the 2,6-bis(dichloromethyl) compound of formula VII and the 2,6-bis(chloromethyl) compound of formula VIII. The invention provides also their production by chlorinating the 2,6-dimethyl compound of formula VI.

The invention also provides as a new compound the 2,6-dimethyl compound of formula VI where R represents —SO$_2$CH$_3$, i.e. the compound 2,6-xylyl methanesulphonate.

The invention provides also a process for preparing the 2,6-dimethyl compound of formula VI, which process comprises reacting 2,6-xylenol (2,6-dimethylphenol) or a salt thereof, with:

(a) a chloride of formula RCl; or
(b) where R represents an acyl group, the acid anhydride R$_2$O.

The invention provides also a process for preparing the isophthalaldehyde of formula

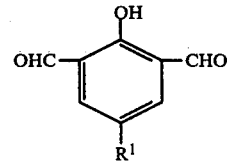

or a salt thereof, where $R^1$ represents alkyl of up to 10 carbon atoms, which process comprises:

(a) oxidising a 2,6-bis(hydroxymethyl)phenol of formula

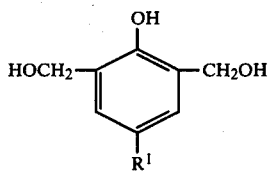

or a salt thereof; or (b) reacting a 2,6-bis(chloromethyl)phenol of formula

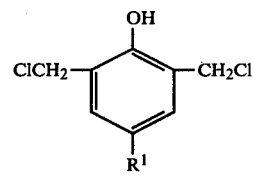

or a salt thereof, to convert the chloromethyl groups to CHO groups.

The invention also provides a process for preparing the 2,6-bis(chloromethyl)phenol of formula X or salt thereof, which process comprises chlorinating the 2,6-bis(hydroxymethyl)phenol of formula IX or salt thereof.

The 2,6-bis(hydroxymethyl)phenol of formula IX or salt thereof can be prepared from the 4-alkylphenol of formula

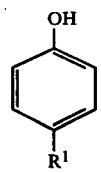

or a salt thereof.

The pyrogallol compound of formula I, e.g. pyrogallol itself, the carbonyl compound of formula II, phenol, 2,6-xylenol, the 2,6-bis(hydroxymethyl)phenol of formula IX, the 2,6-bis(chloromethyl)phenol of formula X and the 4-alkylphenol of formula XI form salts. The compounds can be produced in the form of their salts in the present invention and those compounds which are used as reactants can be employed in the form of their salts.

The salts include particularly alkali metal, e.g. sodium or potassium, especially sodium, salts and can be prepared from the non-salt forms in ways known in themselves, e.g. by reaction with alkali metal alkoxides. The non-salt forms can also be prepared from their salts in ways known in themselves, e.g. by reaction with acid, for example, hydrochloric acid.

Where a product is first formed as a salt and the product is to be employed in a subsequent reaction under basic conditions, it is often convenient to employ the salt form of the product directly in the subsequent reaction rather than convert it to the non-salt form and employ that. Usually pyrogallol itself is first formed in the dealkylation of the pyrogallol compound of formula III or salt thereof, but the pyrogallol can be converted to its salt if desired though this is not preferred. In the oxidation of the carbonyl compound of formula II or a salt thereof, the pyrogallol compound of formula I may be produced as itself or as a salt, depending for instance on whether the carbonyl compound or a salt thereof is employed and how much base is added. When a salt is formed initially, it is preferably converted to the pyrogallol compound itself.

In the oxidation of the 2,6-bis(hydroxymethyl)phenol of formula IX or a salt thereof, the isophthalaldehyde of formula V may initially be formed as a salt. This can be converted to the isophthalaldehyde itself.

The conversion of the 4-alkylphenol of formula XI or a salt thereof may initially produce the 2,6-bis(hydroxymethyl)phenol of formula IX as a salt. This can be converted to the 2,6-bis(hydroxymethyl)phenol itself.

In the present compounds $R^1$ usually represents a hydrogen atom, alkyl of up to 10 carbon atoms, carboxy or alkoxycarbonyl of 2-5 carbon atoms. Preferably $R^1$ represents a hydrogen atom or alkyl of up to 10 carbon atoms. The alkyl group may be for example of up to 8 carbon atoms. The alkyl group is preferably a secondary or tertiary alkyl group, especially a tertiary alkyl group, particularly t-butyl.

$R^5$ usually represents a hydrogen atom, alkyl of 1-4 carbon atoms or phenylalkyl of 7-10 carbon atoms. Where there are two $-COR^5$ groups in a compound, these may be the same or different. $R^5$ preferably represents a hydrogen atom.

In the present compounds, $R^1$ is preferably para to $R^3$.

In the carbonyl compound of formula II, preferably $R^3$ represents —OH, and $R^2$ and $R^4$ represent the same or different —$COR^5$ group.

Preferably a pyrogallol compound of formula III, or a salt thereof, where $R^1$ represents a hydrogen atom or alkyl of up to 10 carbon atoms is prepared by oxidising an isophthalaldehyde of formula

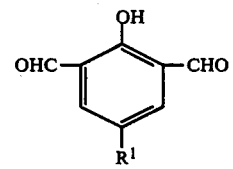

or a salt thereof.

The conversion of the carbonyl compound of formula II, or a salt thereof, to the pyrogallol compound of formula I, or a salt thereof, is an oxidation, but a special type of oxidation, in which one or two —$COR^5$ groups are converted to OH groups. Such a conversion is known as the Dakin reaction, and the present reaction can be carried out under known conditions for a Dakin reaction.

The oxidation is preferably carried out by reaction with a peroxy compound. The peroxy compound is preferably a peroxide (e.g. an alkali metal or alkaline earth metal peroxide or hydrogen peroxide) or a peroxy acid or salt (e.g. alkali metal or alkaline earth metal salt) thereof. The peroxy acid may be for example peracetic acid or Caro's acid (of formula $HO.SO_2OOH$). The peroxide may be for example barium peroxide, benzoyl hydrogen peroxide or sodium peroxide. It is especially preferred that the peroxy compound is hydrogen peroxide.

The hydrogen peroxide is generally admixed as an aqueous solution containing 1–50%, preferably 5–25%, H$_2$O$_2$. Percentages in this specification are by weight unless otherwise indicated.

The concentration of the peroxy compound in the reaction medium is generally from 0.1 to 20%, usually from 0.1 to 10%.

The peroxy compound reacts in the stoichiometric proportions of one —O—O— group per —COR$^5$ group. An excess of peroxy compound may be employed. Generally, 0.5–5, preferably 0.8–2.5, moles of peroxy compound are employed per mole of the carbonyl compound of formula II or salt thereof.

The reaction may be carried out for example at a pH of 0–12, e.g. 0–9, preferably between 7 and 9. Preferably the reaction is carried out under basic conditions. Thus, in a preferred embodiment, pyrogallol or a salt thereof is prepared by a process comprising reacting 2-hydroxyisophthalaldehyde or a salt thereof with hydrogen peroxide under basic conditions. In another preferred embodiment, a pyrogallol compound of formula III or a salt thereof, where R$^1$ represents a secondary or tertiary alkyl group of up to 10 carbon atoms, is prepared by a process comprising reacting an isophthalaldehyde of formula V or a salt thereof, with hydrogen peroxide under basic conditions.

To make the reaction medium acid, an acid such as sulphuric acid, formic acid or acetic acid may be employed.

Base employed to make the reaction medium basic may be inorganic or organic. The organic base may be for example pyridine or a quaternary base, e.g. a quaternary ammonium base such as tetramethylammonium hydroxide or benzyl trimethyl ammonium hydroxide. Preferably, however, the base is inorganic, such as ammonium hydroxide, an alkali metal (especially sodium or potassium) hydroxide, carbonate or bicarbonate or an alkaline earth metal (particularly calcium, strontium or barium) hydroxide. In a preferred embodiment, the base is sodium hydroxide or potassium hydroxide.

The amount of acid or base is that required to provide the required pH. If one starts with a salt of the carbonyl compound of formula II, e.g. an isophthalaldehyde of formula V, one may react without any added base, but then reaction, e.g. when R$^1$ represents a hydrogen atom, may not be complete. Hence, whether one starts with the carbonyl compound or a salt thereof, it is preferred to add base.

The reaction releases acid, e.g. formic acid when R$^5$ represents a hydrogen atom, and preferably sufficient base is present to react with it.

Excess base may be employed, especially when the base, e.g. pyridine, is also being employed as solvent. Generally, however, 0.3–5 moles of base are employed per mole of carbonyl compound or salt thereof, e.g. 2–5 moles when the carbonyl compound itself is employed, and 1–4 moles when a salt of the carbonyl compound is employed.

Usually water is employed as solvent in the reaction, though additional solvents, e.g pyridine, can be admixed therewith.

The reaction may be carried out for example at a temperature of 0°–200° C., preferably 0°–140° C., e.g. 0°–85° C., especially 4°–50° C. Ambient temperature or slightly below is preferred.

The carbonyl compound of formula II or salt thereof can be supplied to the reaction medium in the form of a carbonyl derivative of the —CO group or groups, e.g. a bisulphite derivative, but this is not preferred since the derivative is converted to the carbonyl compound or salt thereof itself under the reaction conditions.

Pyrogallol compounds, e.g. pyrogallol itself, and their salts tend to absorb oxygen which decomposes them, particularly under basic conditions. It is therefore very surprising that the carbonyl compound of formula II or a salt thereof can be oxidised to the pyrogallol compound of formula I, e.g. pyrogallol itself, or a salt thereof, especially when this is done under basic conditions. It is also surprising that the reaction can be applied to the compounds containing two —COR$^5$ groups, e.g. two —CHO groups, and only a single OH group.

The reaction is also particularly useful since the oxidising agents, e.g. hydrogen peroxide, produce little effluent and do not involve by-product problems.

When a pyrogallol compound of formula I or a salt thereof is produced in which R$^1$ represents other than a hydrogen atom, this preferably is then converted to the pyrogallol compound of formula I or a salt thereof in which R$^1$ represents a hydrogen atom, i.e. to pyrogallol or a salt thereof itself. The conversion can be carried out in known ways or in ways known for related compounds.

When R$^1$ represents carboxy, the conversion to R$^1$ representing a hydrogen atom may be carried out by heating e.g. at 50°–200° C., usually in the absence of solvent. When R$^1$ represents alkoxycarbonyl, the conversion may be carried out by hydrolysing this R$^1$ group to carboxy, e.g. by acid or alkaline hydrolysis at 50°–150° C., and then proceeding as described for the case in which R$^1$ represents carboxy.

When R$^1$ represents alkyl, the conversion to R$^1$ representing a hydrogen atom is dealkylation. It may be carried out for example by heating for instance at 50°–350° C., preferably 100°–200° C. Preferably it is carried out in the presence of a dealkylation catalyst for example hydrobromic acid, hydrogen chloride, sulphuric acid, an alkyl sulphuric acid ester, tetraphosphoric acid, a sulphonic acid (e.g. p-toluenesulphonic acid), activated clay, a metal oxide (e.g. gamma alumina), a metal chloride (e.g. aluminium chloride or ferric chloride), a molecular compound of aluminium chloride with a phenol or alcohol, or a sulphonic acid cation exchange resin (e.g. Amberlite). For example, the catalyst may be hydrogen chloride at high temperature e.g. 200–300 such as 250° C. and under pressure, attapulgous clay at 275°–350° C. or acid activated Fuller's Earth e.g. at 100°–300° C. Preferred catalysts which effect the dealkylation include concentrated sulphuric acid or p-toluene sulphonic acid, both suitably at 150°–200° C. Another preferred catalyst is aqueous hydrobromic acid. Constant boiling aqueous hydrobromic acid is suitable. The reaction with hydrobromic acid is usually carried out by heating e.g. at a temperature of 50°–120° C., preferably by boiling under reflux.

The weight of catalyst may be for example 1–35% of weight of the substance being dealkylated.

The dealkylation catalyst may advantageously be a solid catalyst such as acid activated Fuller's Earth or gamma alumina.

In a surprising feature provided by the present invention, the dealkylation catalyst comprises sulphuric acid, p-toluenesulphonic acid, ferric chloride, acid activated Fuller's Earth, aluminium chloride or zinc chloride. The Fuller's Earth may be in admixture with hydrochloric acid.

In a particularly surprising feature provided by the present invention, the dealkylation is effected by reaction with phenol or a salt thereof, preferably phenol, in the presence of a dealkylation catalyst. The phenol or salt thereof is preferably used in excess, its weight being for example between 1 and 10 times the weight of the substance being dealkylated. The dealkylation catalyst may be any of those described above, and may be employed in the amount described above. Acid activated Fuller's Earth, sulphonic acid cation exchange resin, or aluminium chloride, especially acid activated Fuller's Earth, however, are especially advantageous as dealkylation catalyst for this technique.

It is believed that in this dealkylation with phenol or a salt thereof, the phenol or salt thereof is converted to the 4-alkylphenol of formula XI in which $R^1$ represents alkyl, or a salt thereof. Thus, an alkyl transfer reaction could be considered as occurring.

The dealkylation with phenol or a salt thereof is particularly convenient and gives a suprisingly high yield.

The pyrogallol compounds of formula I, e.g. pyrogallol itself, and especially their salts absorb oxygen and hence decompose when hot and the salts absorb oxygen and hence decompose even at ambient temperature. Accordingly in air it is preferred to minimise the use of their salts and to employ as low a temperature as will effect satisfactorily the required production of the compounds or their salts, e.g. by oxidation. For the same reason, the production may be effected in an inert atmosphere, e.g. an atmosphere of nitrogen, if desired.

Instead of oxidising an isophthalaldehyde of formula V where $R^1$ represents alkyl, or a salt thereof, to a pyrogallol compound of formula III having this $R^1$ group, or a salt thereof, and dealkylating this pyrogallol compound or salt thereof to pyrogallol itself or a salt thereof, one can dealkylate the isophthalaldehyde or salt thereof to remove the $R^1$ group, in an analogous way to the dealkylation described above, and then oxidise the 2-hydroxyisophthalaldehyde or salt thereof to pyrogallol or salt thereof.

The purpose of the protectant group R in the compounds of formulae VI, VII and VIII is to enable their —CH$_3$, —CHCl$_2$ or —CH$_2$Cl groups to be converted to —CHO groups while avoiding the decomposition which tends to occur if the unprotected material is employed, e.g. oxidised directly or chlorinated. Preferably R represents —COCl, —CO alkyl, or —COOR' or —SO$_2$R' where R' represents alkyl, aryl or aryl substituted preferably mono- or di-substituted by alkyl or haloalkyl. The 'alkyl' groups are preferably of 1-4 carbon atoms especially methyl, the 'aryl' is preferably phenyl and the 'haloalkyl' is preferably of 1-4 carbon atoms, especially methyl, mono- or di-substituted by chlorine. For example, R' may be p-tolyl or 2,6-xylyl. R can be the same in formula VI as it is in formula VII or VIII or it may be chlorinated as well as the methyl groups attached to the benzene ring in formula VI when the 2,6-dimethyl compound of formula VI is converted to the 2,6-bis(dichloromethyl) compound of formula VII or the 2,6-bis(chloromethyl) compound of formula VIII by chlorination. Thus, the compound of formula VI may be bis(2,6-xylyl) carbonate and this may be converted to

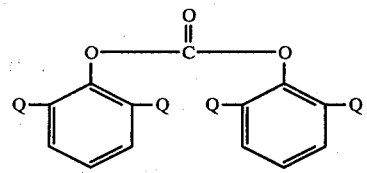

where each Q is the same and represents CH$_2$Cl or CHCl$_2$, and this converted to 2-hydroxyisophthalaldehyde or a salt thereof. Of particular interest is R representing —COCl or —SO$_2$CH$_3$. Most preferred is R representing —COCl.

The 2,6-dimethyl compound of formula VI may be converted into 2-hydroxyisophthalaldehyde or a salt thereof by direct oxidation, e.g. using the Thiele reagent (see Fieser 'Reagents for Organic Chemistry', volume 1 page 146), and removal of the protectant group R. Preferably, however, the conversion is effected indirectly, via the 2,6-bis(dichloromethyl) compound of formula VII or the 2,6-bis(chloromethyl) compound of formula VIII.

The conversion of the chlorinated compounds VII and VIII to 2-hydroxyisophthalaldehyde or a salt thereof involves (A) removal of the protectant group by converting OR to OH, and (B) conversion of each chlorinated side chain to the group —CHO. This may be carried out as two separate stages corresponding to (A) and (B). Thus, starting from the bis(dichloromethyl) compound of formula VII, one may first remove the protectant group to form 2,6-bis(dichloromethyl)-phenol or a salt thereof. Again, starting from the bis(chloromethyl) compound of formula VIII one may first remove the protectant group to form 2,6-bis(chloromethyl)phenol or a salt thereof.

Preferably, however, the conversion of the chlorinated compounds VII and VIII to 2-hydroxyisophthalaldehyde or a salt thereof is accomplished in a single stage. 2,6-Bis(dichloromethyl)phenol or a salt thereof or the bis(dichloromethyl) compound of formula VII can be converted to 2-hydroxyisophthalaldehyde or a salt thereof by a process comprising hydrolysis. Acid hydrolysis can be employed, e.g. using sulphuric acid. Preferably, however, alkaline hydrolysis is employed, e.g. using calcium carbonate; this may form a salt of 2-hydroxyisophthalaldehyde initially, and this is preferably converted to 2-hydroxyisophthalaldehyde itself by treatment with acid e.g. hydrochloric acid. A temperature of 10°-110° C. may be used for the hydrolysis. 2,6-Bis(chloromethyl)phenol or a salt thereof or the bis(chloromethyl) compound of formula VIII can be converted to 2-hydroxyisophthalaldehyde or a salt thereof by a process comprising the Sommelet reaction, i.e. reaction with hexamethylenetetramine followed by heating with water (conveniently aqueous ethyl alcohol), e.g. at a temperature of 60°-100° C. The usual reaction conditions for a Sommelet reaction may be employed. When the bis(chloromethyl) compound of formula VIII is employed in the Sommelet reaction, the protectant group R is usually removed automatically in the stage of heating with water. If it is not, a separate removal step can be carried out.

The chlorinated compounds VII and VIII may be obtained by chlorinating the 2,6-dimethyl compound of formula VI. Chlorine gas is preferably employed, e.g. at a temperature of 100°-200° C. until the desired uptake of chlorine has occurred. In order to avoid decomposition during the chlorination, the 2,6-dimethyl compound should be substantially free from free phenol and this can be achieved by thorough alkali washing.

The 2,6-dimethyl compound of formula VI can be prepared from 2,6-xylenol or a salt thereof by ways known for related compounds. Generally, e.g. when R represents —COCl or an acyl group such as —CO alkyl or —SO$_2$R', the dimethyl compound of formula VI can be prepared by reaction with RCl. Alternatively, e.g. when R represents an acyl group such as —CO alkyl or —SO$_2$R', the dimethyl compound of formula VI may be prepared by reaction with R$_2$O. The reactions may be conducted in an inert solvent, e.g. a hydrocarbon or chlorinated hydrocarbon such as toluene or carbon tetrachloride. The reactions may for instance be conducted at a temperature of 0°–150° C.

The oxidation of the 2,6-bis(hydroxymethyl)phenol of formula IX or a salt thereof may be carried out at a temperature of e.g. 50°–110° C. The oxidation can be effected by dimethylsulphoxide, e.g. by heating up to reflux temperature; active manganese dioxide (see for example JOC 35 (1970) 3971), e.g. by agitating a benzene solution with the active manganese dioxide; or chromium trioxide as the Jones reagent CrO$_3$/H$_2$SO$_4$ (see for example JCS, 1946, 43) or as the Collins reagent CrO$_3$/pyridine (see for example JOC, 35 (1970) 4001). Since it gives a product of good purity in high yield, however, it is preferred to use sodium m-nitrobenzenesulphonate, for example at a temperature of 50–100 e.g. 80° C., and in aqueous solution preferably under alkaline conditions.

The oxidation of the 2,6-bis(hydroxymethyl)phenol of formula IX or salt thereof can be carried out in 2 stages, e.g. via the 2,6-bis(chloromethyl)phenol of formula X or salt thereof when R$^1$ represents alkyl of up to 10 carbon atoms.

The 2,6-bis(chloromethyl)phenol of formula X or a salt thereof can be converted to the isophthalaldehyde of formula V or a salt thereof by a process comprising the Sommelet reaction which is described above.

The 2,6-bis(chloromethyl)phenol of formula X or a salt thereof can be prepared by a process comprising chlorinating, e.g. by thionyl chloride, the 2,6-bis(hydroxymethyl)phenol of formula IX or a salt thereof.

The 2,6-bis(hydroxymethyl)phenol of formula IX or a salt thereof is generally known and can be prepared in known ways, in particular from the 4-alkylphenol of formula XI in which R$^1$ represents alkyl of up to 10 carbon atoms, or a salt thereof. For instance, the 4-alkylphenol or salt thereof can be converted to the 2,6-bis(hydroxymethyl)phenol of formula IX or a salt thereof by reaction with formaldehyde and sodium hydroxide.

The present reactions are usually conducted in inert solvents except as noted above. Normally, the reactions are conducted at ambient pressure, though a pressure of e.g. 0.5–10 atmospheres may be employed. Where a temperature has not been specified for a reaction above, it may be carried out for example at 0°–200° C., preferably 0°–150° C.

A particularly useful feature of the present invention is the provision of 2-hydroxyisophthalaldehyde or a salt thereof from 2,6-xylenol or a salt thereof by a sequence of reactions referred to above.

Outstandingly useful is the provision of pyrogallol or a salt thereof from 2,6-xylenol or a salt thereof by the sequence of reactions:

(a) reacting 2,6-xylenol, or a salt thereof, with the chloride of formula RCl or with the acid anhydride R$_2$O, to produce the 2,6-dimethyl compound of formula VI;

(b) reacting the 2,6-dimethyl compound of formula VI to oxidise the CH$_3$ groups to CHO and to convert the OR group to OH, and thus produce 2-hydroxyisophthalaldehyde or a salt thereof; and (c) oxidising the 2-hydroxyisophthalaldehyde or a salt thereof.

Also outstandingly useful is the provision of pyrogallol or a salt thereof by the sequence of reactions:

(a) converting the 4-alkylphenol of formula XI where R$^1$ represents alkyl of up to 10 carbon atoms, or a salt thereof, to the 2,6-bis(hydroxymethyl)phenol of formula IX or salt thereof;

(b) oxidising the 2,6-bis(hydroxymethyl)phenol of formula IX or salt thereof to the isophthalaldehyde of formula V or salt thereof;

(c) oxidising the isophthalaldehyde of formula V or salt thereof to the pyrogallol compound of formula III or a salt thereof; and (d) dealkylating the pyrogallol compound of formula III or salt thereof to remove the R$^1$ group. When phenol or a salt thereof is converted to the 4-alkylphenol of formula XI or a salt thereof in the final stage (d), as discussed above, the 4-alkylphenol or salt thereof can be used in the first stage (a), and this is particularly advantageous.

Pyrogallol produced in the present invention is particularly suitable for use as an intermediate in the production of the insecticide 2,2-dimethyl-1,3-benzodioxol-4-yl methylcarbamate. This can be produced by reacting the pyrogallol with 2,2-dimethoxypropane to form 2,2-dimethyl-4-hydroxy-1,3-benzodioxole, and reacting this with methyl isocyanate.

The invention is illustrated by the following Examples, in which parts and percentages are by weight unless otherwise indicated.

EXAMPLE 1

244 Parts of 2,6-xylenol (the material available commercially from Synthetic Chemicals Limited and containing at least 92% 2,6-xylenol) were dissolved in 1595 parts of carbon tetrachloride and to this solution were added 297 parts of phosgene, the temperature being maintained below 5° C. To this solution was added 108 parts of sodium hydroxide dissolved in 467 parts of water. The time of addition was 1 hour, the temperature being maintained below 10° C. After separation of the aqueous layer, a further wash with a solution of 108 parts of sodium hydroxide dissolved in 467 parts of water was given. Examination of the organic phase showed that free phenolic material was still present. This was removed by agitating with a further wash of 36 parts of sodium hydroxide dissolved in 430 parts of water.

The organic layer was removed and dried with anhydrous sodium sulphate. After evaporation to remove carbon tetrachloride, 221.8 parts of 2,6-dimethylphenyl chloroformate (chloroformic acid, 2,6-xylyl ester) were obtained. This material was purified by distillation under vacuum, giving 185 parts of purified product, boiling point 100° C. at 20 mm.

EXAMPLE 2

183.6 Parts of the purified material from Example 1 above was chlorinated by chlorine gas at 150°–165° C., until a gain in weight of 138.4 parts was obtained (equivalent to an average of 3.92 chlorine atoms per molecule). The deep red-brown oil obtained was fractionally distilled to give a main fraction boiling point 180°–182° C. at 20 mm; yield 220.4 parts. A sample of this product was analysed for carbon, hydrogen, and chlorine:

Found: C: 33.13; H: 1.20; Cl: 55.28%; $C_9H_5Cl_5O_2$ requires: C: 33.53; H: 1.56; Cl: 54.99%.

The product is 2,6-bis(dichloromethyl)phenyl chloroformate.

EXAMPLE 3

97 Parts of the chlorinated product from Example 2 were refluxed with 375 parts of water and 112.5 parts of finely powdered calcium carbonate for 23 hours. The reaction was mechanically agitated.

The reaction mixture was steam distilled to give 1,000 parts of distillate which was discarded. The residue was acidified with an excess of concentrated aqueous hydrochloric acid and steam distilled until no further product was obtained. The steam distillate was extracted with ether and the ether dried with anhydrous sodium sulphate. Evaporation of the ether solution gave 28.1 parts of product which was identified as 2-hydroxyisophthalaldehyde by its infra red and nuclear magnetic resonance spectra.

EXAMPLE 4

The 2-hydroxyisophthalaldehyde of Example 3 was converted to pyrogallol by the Dakin reaction.

The reaction was carried out in an atmosphere of nitrogen up to the end of the continuous ether extraction.

47.3 Parts of 25.9% hydrogen peroxide solution were agitated at 5°–10° C. with 420 parts of water. A solution of 15 parts of 2-hydroxyisophthalaldehyde, prepared in Example 3 above, in a mixture of 20 parts of 85% potassium hydroxide in 250 parts of water was added over 45 minutes using external cooling to maintain this temperature and avoid large temperature variations. After agitating for a further 2.5 hours at 5°–10° C., when pyrogallol was present probably largely as its potassium salt, the pH of the solution was adjusted to 6.5 and the solution was continuously extracted at ambient temperature with ether. After drying the ether extract with anhydrous sodium sulphate it was evaporated to low bulk and a small amount of precipitated impurities were removed by filtration. Evaporation of the filtrate gave 8.1 parts of pyrogallol.

EXAMPLE 5

12.5 Parts of methanesulphonyl chloride and 11.0 parts of triethylamine were added separately and simultaneously to a solution of 12.2 parts of 2,6-xylenol (the material available commercially from Synthetic Chemicals Limited and containing at least 92% 2,6-xylenol) in 65 parts of toluene over 40 minutes. The reaction mixture was mechanically agitated and the temperature was maintained at 40°–50° C. with external cooling. After agitating for a further 30 minutes, 24 parts of water were added, and the two phase mixture was separated. Evaporation of the organic phase gave 19.7 parts of 2,6-xylyl methanesulphonate. The product was purified by distillation at 188°–191° C. at 30 mm. On cooling the ester solidified, remelting at 26°–27° C.

EXAMPLE 6

20 Parts of 2,6-xylyl methanesulphonate were treated with a stream of dry chlorine gas at 160°–180° C. until a weight gain of 14 parts was obtained. The crude chlorinated material was obtained as a pale orange viscous liquid.

EXAMPLE 7

6.76 Parts of crude product from Example 6 above were dissolved in 21 parts of ethyl alcohol and to this solution 7.7 parts of 47% by weight sodium hydroxide solution was added over 25 minutes, the temperature being maintained at 10°–20° C. with external cooling. After mixing for a further 15 minutes, the pH was adjusted to 5.0 with hydrochloric acid and the solution extracted with ether. The ether extract was washed with 3 portions of dilute sodium hydroxide solution, dried with anhydrous sodium sulphate, and evaporated to give 5.12 parts of crude product.

EXAMPLE 8

The reaction was carried out in an atmosphere of nitrogen up to the ether extraction stage.

1.64 Parts of crude product from Example 7 were dissolved in a solution of 2 parts of potassium hydroxide (85%) in 25 parts of water. To this solution was added 14 parts of 5% hydrogen peroxide solution, the temperature being maintained at 10°–15° C. Pyrogallol was present, largely as its potassium salt. After acidification, the solution was continuously extracted with ether giving, on evaporation, 1.4 parts of crude product which was shown to contain pyrogallol by gas liquid chromatography.

EXAMPLE 9

A two-phase reaction mixture was prepared from 24.4 parts of 2,6-xylenol and 160 parts of carbon tetrachloride and a solution of 21.1 parts of sodium carbonate with 8 parts of sodium hydroxide dissolved in 108 parts of water. 3.2 Parts of tetrabutylammonium bromide were added and, with mechanical agitation, phosgene was introduced at 18°–22° C. When the total phosgene uptake was 11.1 parts, the rate of absorption dropped, and the organic phase was washed with water, dried with anhydrous sodium sulphate and evaporated, to give 16.9 parts of material identified as bis(2,6-xylyl) carbonate by comparison of its infra red spectrum with that of authentic material.

EXAMPLE 10

10 Parts of the purified material from Example 1 was chlorinated by chlorine gas at 160°–170° C. until a gain of 4.0 parts was obtained. The chlorination time was 4 hours. The crude reaction product was then distilled to give a main fraction boiling point 155°–175° C. at 20 mm; yield 12.0 parts. This material deposited crystals on standing, which were separated and recrystallised from petroleum ether giving solid of melting point (m.pt.) 67.5°–69.5° C. A sample of this crystalline material was analysed for carbon, hydrogen and chlorine:

Found: C: 42.3; H: 2.7; Cl: 41.9%; $C_9H_7Cl_3O_2$ requires: C: 42.6; H: 2.8; Cl: 42.0%.

The product is 2,6-bis(chloromethyl)phenyl chloroformate.

EXAMPLE 11

9.0 Parts of the product of Example 10 were added rapidly to a refluxing solution of hexamine (20.0 parts in tetrachloroethylene (250 parts by volume). A white solid rapidly precipitated. After refluxing for 1 hour the solid was filtered off and added to 150 parts by volume of 60% by volume aqueous ethyl alcohol. After refluxing for 0.5 hours, 25 parts by volume of concentrated hydrochloric acid was added and the refluxing continued for a further 0.1 hours. The product was isolated by steam distillation and ether extraction of the distillate to give 0.1 parts of 2-hydroxyisophthalaldehyde, m.pt. 122°–125° C.

EXAMPLE 12

21 Parts of 2,6-bis(hydroxymethyl)-4-tert-butylphenol, m.pt. 62°–63° C., was added to a solution of 16.5 parts of sodium hydroxide in 150 parts of water. To the resulting mixture was added 107 parts of sodium m-nitrobenzene sulphonate.

The thick slurry obtained was heated for 14 hours at 80°–90° C. with mechanical agitation. After standing at ambient temperature for 3 days, the yellow insoluble sodium salts were filtered off and added to 850 parts of water. The small amount of insoluble material was removed by filtration and the filtrate was acidified to give a pale yellow precipitate of 5-tert-butyl-2-hydroxyisophthalaldehyde. This was filtered off and air dried to yield 14.7 parts of product (71% yield), m.pt. 101°–103° C.

EXAMPLE 13

Under a nitrogen atmosphere throughout:

A solution of 2.06 parts of the 5-tert-butyl-2-hydroxyisophthalaldehyde prepared in Example 12 in 27 parts of 6.5% potassium hydroxide solution was added to 37.5 parts of 3% hydrogen peroxide solution over 25 minutes. The temperature was maintained between 4° and 8° C., with external cooling. After adjustment of the pH to 6.4, the reaction mixture was filtered and the filtrate continuously extracted with ether. The ether was dried with sodium sulphate and evaporated to give a red oil. The oil was redissolved in 60 parts of water, the pH adjusted to 6.9, and continuously extracted with ether as before. Evaporation of the dried ether extract gave 0.9 parts of cream solid m.pt. 134°–139° C., equivalent to 50% yield of 5-tert-butylpyrogallol.

EXAMPLE 14

33.6 Parts of 2,6-bis(hydroxymethyl)-4-methylphenol, m.pt. 126°–128° C., were slurried with 112 parts of chloroform, and 71.2 parts of thionyl chloride were added over 18 minutes at 30°–35° C. After agitating at ambient temperature for a further 53 minutes, the volatile materials were removed by distillation to maximum liquid temperature 90° C. at 20 mm pressure to give a dark liquid which solidified to give a solid m.pt. 72°–79° C. Recrystallisation from iso-octane gave solid m.pt. 77°–82° C. This material was identified as 2,6-bis(chloromethyl)-4-methylphenol on the basis of its infra red spectrum.

EXAMPLE 15

A solution of 20.1 parts of hexamine in 187 parts of chloroform was added to a solution of 13.6 parts of the product of Example 14 in 37 parts of chloroform at ambient temperature. The temperature rose to 50° C., and white solid precipitated immediately. After leaving for sixteen hours, the solid was filtered off, washed with chloroform and dried to give 35 parts of crude product. This product was refluxed with 127 parts of 50% acetic acid for 1.75 hours, diluted with 65 parts of water and cooled. Yellow 2-hydroxy-5-methylisophthalaldehyde was filtered off and dried. Yield 3.5 g, m.pt. 125°–130° C.

EXAMPLE 16

Example 15 was followed except that the hydrolysis was carried out using 6% hydrochloric acid, giving product m.pt. 128°–130° C.

EXAMPLE 17

Under a nitrogen atmosphere throughout: 5.3 Parts of 2-hydroxy-5-methylisophthalaldehyde prepared in Example 15 or 16 were slurried with a solution of 2.6 parts of sodium hydroxide in 32 parts of water, and a solution of 9.8 parts of 27.2% by weight hydrogen peroxide in 35 parts of water was added over four minutes. The temperature rose to 85° C. initially and was then maintained at 40°–50° C. with external cooling. After a further 18 minutes the pH was 7.8. The solution was filtered to remove 1.05 parts of unchanged starting material, and the filtrate was continuously extracted with ether to give 2.5 parts of 5-methylpyrogallol, m.pt. 114°–121° C., equivalent to 69% yield.

EXAMPLE 18

Under a nitrogen atmosphere throughout: 7.2 Parts of 2-hydroxy-5-tertiary-butylisophthalaldehyde were slurried in 20 ml of water, and simultaneous and separate dropwise addition of 20% by weight sodium hydroxide solution and 7.6% weight/volume hydrogen peroxide solution was started with rates of addition to maintain the pH in the range 8.0–9.0. The temperature was maintained in the range 25°–37.5° C. with cooling as required. After 67 minutes, 17.9 ml of the sodium hydroxide solution and 42 ml of the hydrogen peroxide solution had been added. The pH was 8.75. Analysis at this stage by thin layer chromatography showed the presence of a p-tert-butyl phenol. The reaction mixture was filtered to remove some light brown tarry material, and after adjusting the pH to 3.8, the filtrate was extracted once with diethyl ether to give 2.7 parts of crude 5-tert-butylpyrogallol.

EXAMPLES 19–42

In a series of experiments, 5-t-butylpyrogallol (1,2,3-trihydroxy-5-t-butylbenzene) was dealkylated to pyrogallol by heating with the materials specified in the following Table. The Table also records the amounts of material, the reaction time, the reaction temperature and whether the reaction was conducted under an atmosphere of nitrogen. In each experiment, pyrogallol was shown by thin layer chromatography to result. In some cases, the mole percent yield of pyrogallol was assessed, this being done by gas liquid chromatographic analysis. Fulmont XX, Fulmont SQC, Fulmont 22B, Fulcat 14 and Fulcat 15 are acid activated Fuller's Earth. Amberlite IR 120 is a sulphonic acid cation exchange resin.

| Example | Weight in grams of 5-t-Butylpyrogallol | Dealkylation System & Amount | Time, hours | Temperature, °C. | Pyrogallol yield, When Assessed |
|---|---|---|---|---|---|
| 19 | 0.3 | Sulphuric acid, 0.03g | 2 | 140-155 | |
| 20 | 0.3 | P—toluene sulphonic acid, 0.03g | 2 | 140-155 | |
| 21 | 0.3 | Ferric chloride, 0.006g | 1½ | 150 | |
| 22 | 0.3 | Fulmont XX, 0.006g | 4 | 150 | |
| 23 | 0.3 | Aluminium chloride, 0.006g | 3½ | 150 | 7 |
| 24 | 0.3 | Aluminium chloride, 0.006g, + Excess Phenol | 3½ | 150 | |
| 25 | 0.3 | Zinc chloride, 0.006g | 3½ | 150 | 7 |
| 26 | 0.3 | Refluxed with Fulmont XX, 0.1g, + 15 ml concentrated hydrochloric acid | 5 | 108-110 | |
| 27 | 0.3 | Fulmont XX, 0.006g, + Excess Phenol | 2.3 | 1.60 | 18 |
| 28 | 0.3 | Amberlite IR 120 - untreated except for being vacuum dried at 120° C. - 0.006g, + Excess Phenol | 2 | 150 | |
| 29 | 1.87 | Fulmont XX, 0.1g, + Phenol, 1.88g, while maintaining a nitrogen purge | 2½ | 150 | 20.5 |
| 30 | 1.87 | Fulmont XX, 0.1g, + Phenol, 1.88g. Reaction carried out in a tube with an oil seal | 2½ | 150 | 23.1 |
| 31 | 1.87 | Fulmont XX, 0.0374g, + Phenol, 1.88g | 5.8 | 180 | 45 |
| 32 | 1.87 | Fulmont XX, 0.0935g, + Phenol, 1.88g | 5.8 | 180 | 54 |
| 33 | 1.87 | Fulmont XX, 0.187g, + Phenol, 1.88g | 5.8 | 180 | 69 |
| 34 | 1.87 | Fulmont XX, 0.361g, + Phenol, 1.88g | 5.8 | 180 | 55.5 |
| 35 | 1.87 | Fulmont XX, 0.0935g, + Phenol, 1.88g | 4.2 | 150-160 | 38.1 |
| 36 | 1.87 | Fulmont 22B, 0.0935g, + Phenol, 1.88g | 4.2 | 150-160 | 45.2 |
| 37 | 1.87 | Fulcat 14, 0.0935g, + Phenol, 1.88g | 4.2 | 150-160 | 46.8 |
| 38 | 1.87 | Fulcat 15, 0.0935g, + Phenol, 1.88g | 4.2 | 150-160 | 41.3 |
| 39 | 1.87 | Sulphuric acid, 0.037g | 3 | 150 | 12.4 |
| 40 | 1.87 | P—toluene sulphonic acid, 0.037g | 3 | 150 | 14.9 |
| 41 | 1.87 | Aluminium chloride, 0.037g | 3 | 150 | 17.6 |
| 42 | 1.87 | Amberlite IR 120 exchange resin vacuum dried at 120° C., 0.037g | 3 | 150 | 5.2 |

I claim:

1. A process for preparing a pyrogallol compound of the formula

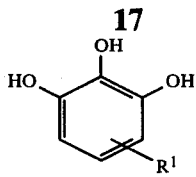
I or a salt thereof, where $R^1$ represents a hydrogen atom, alkyl of up to 10 carbon atoms, carboxy or alkoxycarbonyl of 2–5 carbon atoms, which process comprises oxidising a carbonyl compound of the formula

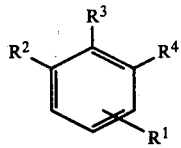
II or a salt thereof, with hydrogen peroxide at a temperature of 0°–200° C. under basic conditions, where $R^1$ is as defined above and $R^2$, $R^3$ and $R^4$ are the same or different and each represents —OH or —COR$^5$, at least one of $R^2$, $R^3$ and $R^4$ representing —OH and at least one of $R^2$, $R^3$ and $R^4$ representing —COR$^5$, where $R^5$ represents a hydrogen atom, alkyl of 1–4 carbon atoms or phenylalkyl of 7–10 carbon atoms, the amount of hydrogen peroxide being 0.5–5 moles per mole of the carbonyl compound.

2. A process according to claim 1 wherein a pyrogallol compound of the formula

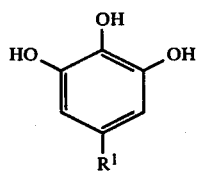
III or a salt thereof is prepared by oxidising a carbonyl compound of the formula

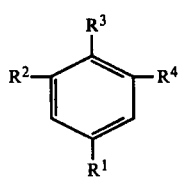
IV or a salt thereof.

3. A process according to claim 1 wherein $R^3$ represents —OH, and $R^2$ and $R^4$ represent the same or different —COR$^5$ group.

4. A process according to claim 1 wherein a pyrogallol compound of the formula

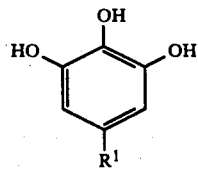
III or a salt thereof, where $R^1$ represents a hydrogen atom or alkyl of up to 10 carbon atoms, is prepared by oxidising an isophthalaldehyde of the formula

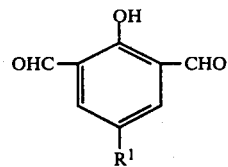
V or a salt thereof.

5. A process according to claim 1 wherein pyrogallol or a salt thereof, is prepared by reacting 2-hydroxyisophthalaldehyde or a salt thereof with hydrogen peroxide under basic conditions.

6. A process according to claim 1 wherein a pyrogallol compound of the formula

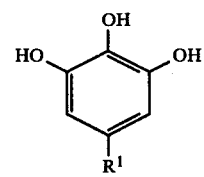
III or a salt thereof, where $R^1$ represents a secondary or tertiary alkyl group of up to 10 carbon atoms, is prepared by reacting an isophthalaldehyde of the formula

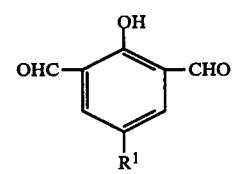
V or a salt thereof, with hydrogen peroxide under basic conditions.

7. A process according to claim 1 wherein the pyrogallol compound or salt thereof is prepared in which $R^1$ represents a group other than a hydrogen atom, and this compound or salt is then converted to pyrogallol or a salt thereof.

8. A process according to claim 1 for preparing pyrogallol or a salt thereof, which process comprises:

(a) reacting 2,6-xylenol, or a salt thereof, with a chloride of the formula RCl where R represents a protecting group, or, where R represents an acyl group, the acid anhydride $R_2O$, to produce a 2,6-dimethyl compound of the formula

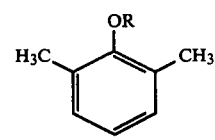
VI where R represents a protecting group, (b) reacting the 2,6-dimethyl compound to oxidise the $CH_3$ groups to CHO and to convert the OR group to OH, to produce 2-hydroxyisophthalaldehyde or a salt thereof, and (c) oxidising the 2-hydroxyisophthalaldehyde or a salt thereof with hydrogen peroxide.

9. A process according to claim 1 for preparing pyrogallol or a salt thereof, which process comprises:
(a) converting a 4-alkylphenol of the formula

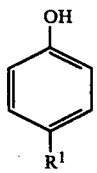  XI or a salt thereof, where $R^1$ represents alkyl of up to 10 carbon atoms, to a 2,6-bis(hydroxymethyl)-phenol of the formula

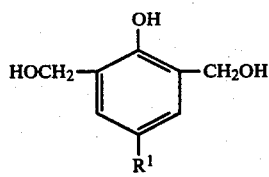  IX or a salt thereof, where $R^1$ as defined above, (b) oxidising the 2,6-bis(hydroxymethyl)phenol or salt thereof to an isophthalaldehyde of the formula

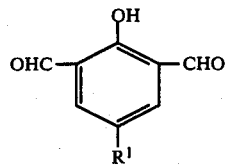  V or a salt thereof, where $R^1$ is as defined above,
(c) oxidising the isophthalaldehyde or salt thereof, with hydrogen peroxide, to a pyrogallol compound of the formula

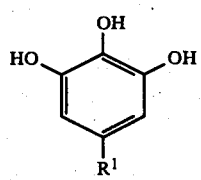  III or a salt thereof, where $R^1$ is as defined above, and
(d) dealkylating the pyrogallol compound or salt thereof to remove the $R^1$ group.

* * * * *